(12) United States Patent
Mansour

(10) Patent No.: US 8,764,442 B2
(45) Date of Patent: Jul. 1, 2014

(54) PRE-CHARGED PROPHY ANGLE

(71) Applicant: Meribel Dental LLC, Balboa Island, CA (US)

(72) Inventor: George Michael Mansour, Pomona, CA (US)

(73) Assignee: Meribel Dental, LLC, Balboa Island, CA (US)

( * ) Notice: Subject to any disclaimer, the term of this patent is extended or adjusted under 35 U.S.C. 154(b) by 0 days.

(21) Appl. No.: 13/943,069

(22) Filed: Jul. 16, 2013

(65) Prior Publication Data

US 2013/0302747 A1 Nov. 14, 2013

Related U.S. Application Data

(63) Continuation of application No. 13/331,846, filed on Dec. 20, 2011.

(51) Int. Cl.
*A61C 17/16* (2006.01)

(52) U.S. Cl.
USPC .............................. 433/84; 433/82; 433/125

(58) Field of Classification Search
USPC .............. 433/80–90, 102–135, 141–142, 166
See application file for complete search history.

(56) References Cited

U.S. PATENT DOCUMENTS

| | | | | |
|---|---|---|---|---|
| 2,400,912 | A * | 5/1946 | Britt et al. | 433/82 |
| 6,257,886 | B1 * | 7/2001 | Warner | 433/125 |
| 7,101,182 | B2 * | 9/2006 | Garrison et al. | 433/125 |

* cited by examiner

*Primary Examiner* — Cris Rodriguez
*Assistant Examiner* — Edward Moran
(74) *Attorney, Agent, or Firm* — Plager Schack LLP

(57) ABSTRACT

A prophy angle is provided that includes a housing with a prophy cup at the distal end, a first drive mechanism positioned within the housing and including a drive shaft for delivering mechanical energy to the prophy cup, a chamber enclosed within the housing to store paste in a controlled releasable manner, and an independent second drive mechanism within the housing to control the delivery of paste from the chamber to the prophy cup in a manner to reduce friction in paste delivery and to avoid contact of the paste with the first drive mechanism and its associated gears.

5 Claims, 3 Drawing Sheets

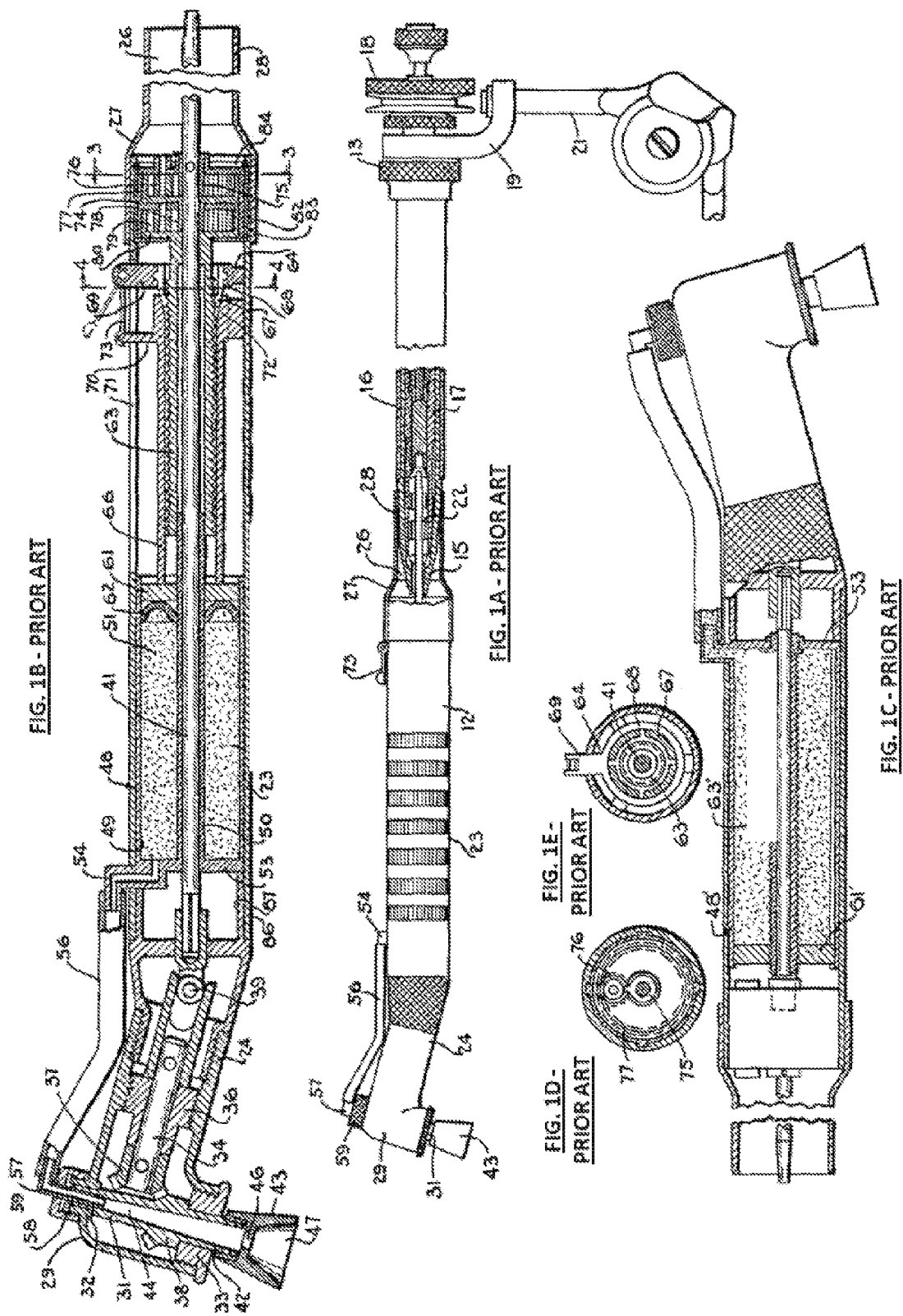

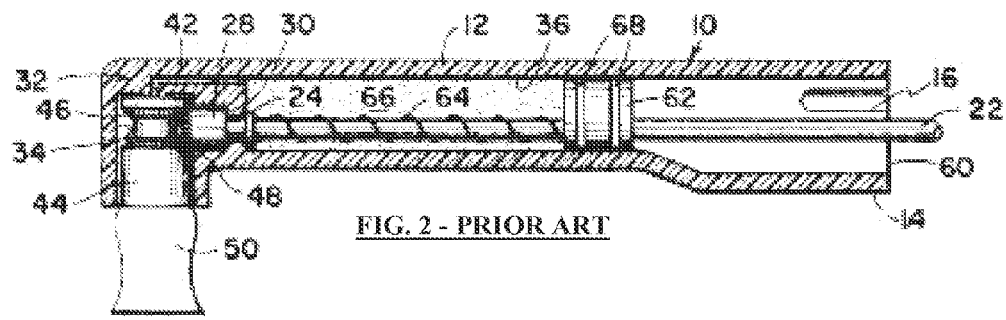
FIG. 2 - PRIOR ART
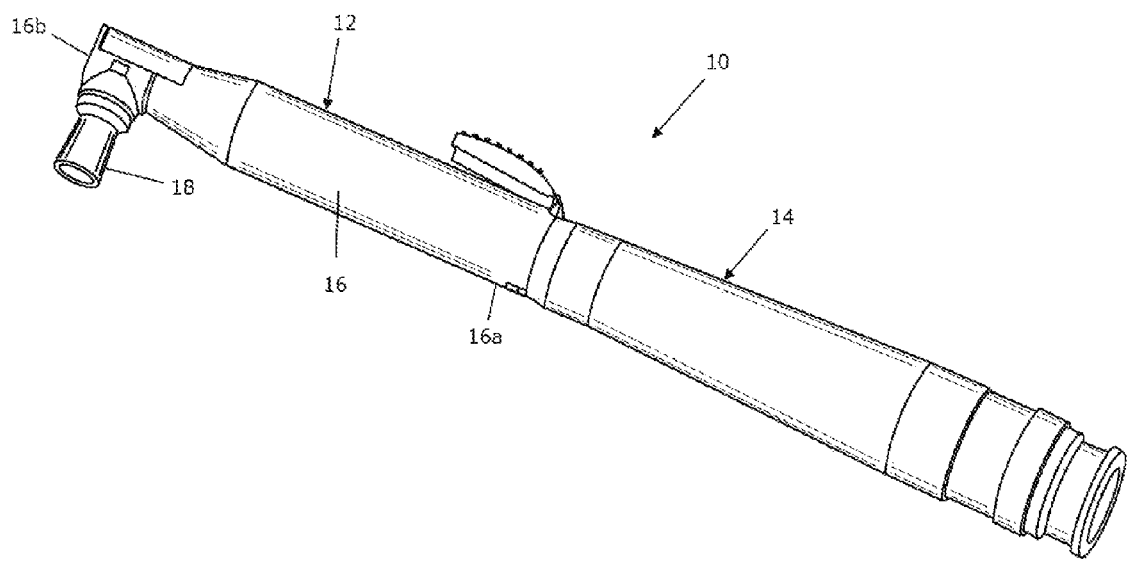
FIG. 3

PRE-CHARGED PROPHY ANGLE

RELATED APPLICATION

This application claims priority to non-provisional patent application U.S. Ser. No. 13/331,846 filed on Dec. 20, 2011, the entire contents of which is herein incorporated by reference.

BACKGROUND

The embodiments herein relate generally to a self-contained prophy angle employing an effective delivery system for dispensing dentifrice in a controlled and economical manner.

A prophy angle is a generally small hand-held device used by dental clinicians to apply therapy to a patient, usually in the form of specially formulated prophy paste for teeth polishing. A rotating cup is often detachably affixed to the distal tip of the prophy angle at an angle to the main longitudinal housing of the prophy angle. The proximal end of the prophy angle is configured as a handle so that the dental clinician, such as a dental hygienist, can exert some comfortable force to polish a patient's teeth with prophy paste applied to the cup.

Traditionally, prophy paste is manually applied to the cup prior to its insertion in the mouth, and then the cup applied to the patient's teeth while power is applied to the device to rotate the cup at a fairly high speed. In that regard, the proximal end of the prophy angle comprises a housing with an opening for accepting therewithin, typically via friction fit, a handle containing a drive mechanism. Historically, the drive mechanism was powered by a tethered drive cable, but since then the drive mechanism comprises a pneumatically-driven motor powered by a tethered air hose. The drive motor is conventionally configured to engage a drive shaft extending from the proximal end of the prophy angle. The drive shaft is axially positioned generally centrally within the prophy angle such that, at a distal end of the drive shaft, a set of bevel gears is typically provided that, in turn, rotatably drive the cup positioned at about an angle normal to the drive shaft.

Over the years, numerous configurations of prophy angles have been presented, with many never becoming commercialized. A prophy angle is intended to be a sturdy but generally light-weight device that is intended for single use only in an effort to address certain infection control issues in the dental practice. Certain bells and whistles have been suggested for the prophy angle over time, but one that has value, but has not yet been commercialized, is a pre-charged prophy angle; i.e., a prophy angle containing a chamber for storing prophy paste and means for discharging the paste as needed. In that regard, numerous patents have been issued on the general scheme of a self-contained prophy angle, including U.S. Pat. No. 2,400,912 to Britt et al.; U.S. Pat. No. 3,389,468 to Lewis, U.S. Pat. No. 3,579,835 to Levenson, U.S. Pat. No. 3,769,707 to Condon, U.S. Pat. No. 3,775,849 to Condon, U.S. Pat. No. 3,987,550 to Danne et al., U.S. Pat. No. 4,220,446 to Walker, U.S. Pat. No. 4,266,933 to Warden et al., U.S. Pat. No. 5,062,796 to Rosenberg, U.S. Pat. No. 5,208,933 to Lustig et al., U.S. Pat. No. 5,642,994 to Chipian et al., U.S. Pat. No. 5,871,353 to Pierce et al., U.S. Pat. No. 5,927,976 to Wu, U.S. Pat. No. 6,632,090 to Randolph, U.S. Pat. No. 7,070,412 to Stadeker, U.S. Pat. No. 7,101,182 to Garrison et al., U.S. Pat. No. 7,160,108 to Jaffe, U.S. Pat. No. Appl. No. 2009-0098505 to Randolph, and PCT Appl. No. WO2009-140630 to Bellanti. None have been known to be successfully commercialized, ostensibly because they are generally not clinically relevant, not cost effective or commercially viable.

By way of specific example, FIG. 1 herein reflects figures from the '912 patent to Britt et al. The disclosed device includes a means of forcing the paste from a chamber to a recess in the tool, which includes a plunger mounted for reciprocation in the chamber that engages the shell and has formed therein a central opening to accommodate the shaft and the shell therearound. With the chamber filled with paste and the plunger in the retracted position, appropriate forward movement of the plunger forces the paste out through the tube and passages. The mechanism of action, as reflected by the arrangement of components in FIG. 1 herein, however, evidences a level of complexity that makes operation inefficient and terribly cost inefficient to manufacture.

By way of an additional example, FIG. 2 herein reflects a figure from the '468 patent to Lewis. There, a housing is disclosed that is pre-charged with a quantity of paste prior to the insertion of a piston within the housing. Rotation of the drive shaft in a direction for moving the piston toward the shoulder forces the paste within the chamber outwardly through the passageway and through the passageway into the interior chamber of the prophy cup. Simultaneously the rotation of the drive shaft rotates the gear that, in turn, transmits rotation to the cup. Among other limitations, the Lewis device suffers from a lack of control of paste discharge, as the action of discharge is controlled by the system driving rotation of the prophy cup. The other prior art prophy angles, even those containing a pre-charging feature, suffer from similar limitations.

As such, a need has arisen for an effective and cost efficient pre-charged prophy angle to meet the dental treatment needs.

SUMMARY

In that regard, embodiments of the present invention satisfy that need by providing an improved self-contained prophy angle that has independent control over the advancement and discharge of prophy paste or the like while simultaneously controlling rotating of the distal prophy cup or other working tool end. In one embodiment, a hand-held oral hygiene applicator or prophy angle is provided comprising a prophy angle housing having a distal end and a proximal end, where the prophy angle housing is configured to permit the clinician to conveniently handle the prophy angle housing at the proximal end while the distal end is placed within a patient's mouth during use. The prophy angle housing is preferably configured to permit the clinician to simultaneously control the expression of paste while providing the desired treatment to the patient.

In one embodiment, the prophy angle comprises a first drive mechanism positioned within the prophy angle housing comprising a drive shaft for delivering mechanical energy to a rotatable head assembly provided at the distal end of the prophy angle housing; a chamber substantially enclosed within the prophy angle housing, the chamber configured to store paste in a controlled releasable manner, the chamber being configured to permit expression of paste by the clinician from the proximal end of the prophy angle housing; and an independent second drive mechanism provided within the prophy angle housing, the second drive mechanism configured to deliver a controlled amount of paste from the chamber to the distal end of the prophy angle housing for as needed expression thereof to the patient by the clinician, the second drive mechanism comprising an actuator positioned at or proximate the proximal end of the prophy angle housing, an index wheel engaging the actuator so that the wheel may be driven in a stepped rotational manner upon actuation of the actuator by the clinician, the index wheel further engaging a barrel within the reloadable chamber, the barrel axially exerting pressure against the paste within the chamber for delivering a controlled quantity of paste toward the distal end of the prophy angle.

In one embodiment, the secondary drive mechanism comprises a shaft comprising helical thread rotatably supporting the barrel, whereby the chamber and helical thread are sized to deliver a pre-set amount of paste for each actuation of the actuator. In another embodiment, the drive shaft of the first drive mechanism is positioned co-linearly with the helical thread and positioned therewithin. In yet another embodiment, the actuator comprises a finger press comprising a member for engaging the index wheel. If desired, the chamber may be configured to be rechargeable for additional use.

BRIEF DESCRIPTION OF THE FIGURES

The detailed description of some embodiments of the invention will be is made below with reference to the accompanying figures, wherein like numerals represent corresponding parts of the figures.

FIGS. 1A through 1E show prior art figures from U.S. Pat. No. 2,400,912 to Britt et al.;

FIG. 2 shows a prior art figure from U.S. Pat. No. 3,389,468 to Lewis;

FIG. 3 is a schematic perspective view of a first embodiment prophy angle;

DETAILED DESCRIPTION OF CERTAIN EMBODIMENTS

Figure 4:
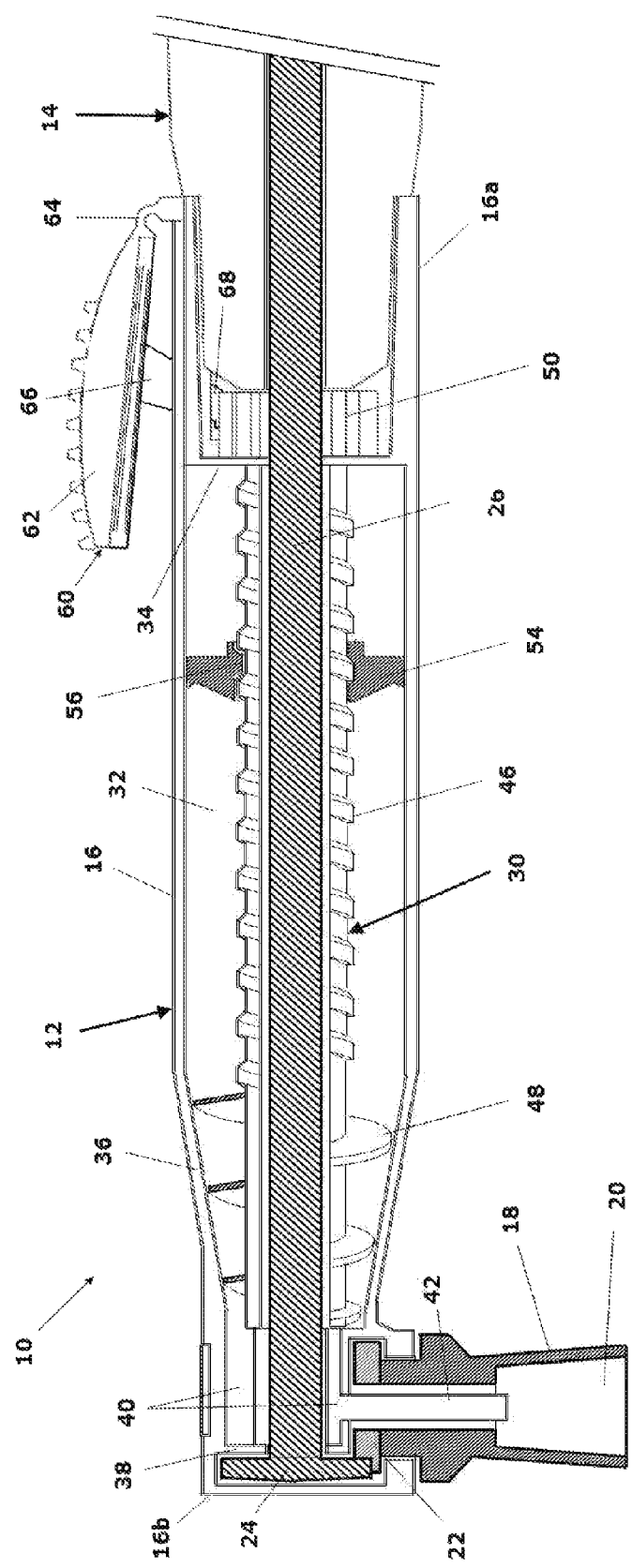
FIG. 4 is a schematic cross-section elevational view of the embodiment of FIG. 3.

By way of example, and referring to FIG. 3, one embodiment of the present invention is a hand-held oral hygiene applicator comprising a self-contained prophy angle 10 comprising a distal member 12 detachably connected to a proximal member 14. The distal member 12 comprises a housing 16 having a proximal end 16a and a distal end 16b supporting a rotatable head assembly or prophy cup 18. The cup 18 may be detachable or fixed to the housing. The proximal member 14 encloses a drive mechanism that is linked directly or indirectly to a power source (not shown). The proximal member 14 further functions to serve as a handle for the dental clinician. The general size and shape may vary from embodiment to embodiment, but it is preferred that the arrangement be such that the prophy angle be configured to permit a user to grasp the proximal member 14 with the hand in a manner to permit an index finger or thumb to be free to exert force upon the distal member 12 for controlled paste expression during use. It is important to note that the invention herein may be used with any type of dentifrice or paste material having therapeutic or non-therapeutic application, depending upon how the dental clinician intends to use embodiments of the invention.

Referring to FIG. 4, the details of the distal member 12 may be appreciated. Provided at the distal end 16b of housing 16 is the prophy cup 18 comprising an internal chamber 20 for discharged paste to accumulate during operation. The prophy cup 18 rotates based upon a drive system, which in one embodiment comprises a first bevel gear 22 engaging a second bevel gear 24 secured to the distal end of a drive shaft 26 that extends axially through the distal member 12. In some embodiments, the drive shaft 26 extends into proximal member 14 by way of friction fit engagement with the drive mechanism (not shown) positioned within the proximal member 14.

In one embodiment, the proximal member 14 is detachably engaged to the distal member 12 via a friction fit, or alternatively within a corresponding connection means within the proximal end 16a of distal member housing 16. In either case, the connection should be made in a manner that the drive mechanism drives the drive shaft 26 so that the prophy cup 18 rotates for dental use. The particulars of the power source and the drive mechanism for the rotating prophy cup are not the subject of the present application. Indeed, one of the benefits of certain embodiments of the present invention is that the drive mechanism for the rotating prophy cup is independent of the self-contained paste-dispensing feature.

In that regard, one embodiment of the present invention comprises a screw shaft 30 rotatably housed within a primary chamber 32 defined at a proximal end by a wall 34 and at the distal end by a tapered portion 36 terminating in a distal wall 38. It should be noted that, although FIG. 4 shows one embodiment generally in elevational cross-section, the screw shaft 30 itself is shown partially in cross-section (above the drive shaft 26) and partially from an external view (below the drive shaft 26) for greater clarity of its configuration in this particular embodiment.

The distal wall 38 partially defines a secondary chamber 40 surrounding the drive shaft 26a in a manner in which the drive shaft is protected from contact with the paste by a surrounding wall. The secondary chamber 40 is fluidly connected to an outlet conduit 42 leading to the dispensing chamber 20 of the prophy cup 18. The secondary chamber 40 and the outlet conduit 42 are configured such that they are not structurally impacted by, and remain stationary during, rotation of the drive shaft and the prophy cup.

The screw shaft 30 comprises an external helical thread 46 positioned along the distal portion of the shaft 30 that is positioned rotatably within primary chamber 32. At the distal portion of the screw shaft 30 is a helical blade 48 that tapers conformingly within the tapered portion 36 of the housing 16. Surrounding the screw shaft is barrel 54 configured to engage the external helical thread 46 of the shaft 30 with a mating internal helical thread 56. With such a configuration, rotation of the screw shaft 30 drives the barrel 54 distally forward in an axial manner; i.e., toward the distal end 16b of the distal member housing 16. The barrel 54 is configured to conform to the internal preferably cylindrical profile of the primary chamber 32 so that any paste stored within the chamber 32 is forced distally (in a quasi stepped plunging action) into the tapered portion 36 of the chamber where the helical blade further drives the paste into the secondary chamber 40 for discharge into the prophy cup chamber 20.

Rotation of the shaft 30 is driven in a controlled fashion by an index wheel or gear 50 that may be indexed radially by manual trigger of dispensing actuation means 60 secured to the proximal housing 16. In one embodiment, the actuation means 60 comprises a finger press 62 preferably ribbed for greater control and rotatably connected to the housing 16 via hinge 64, and is suitable for use with the thumb or index finger. The finger press 62 comprises an extension member 66 that engages at its distal end 68 the gear 50, which preferably has teeth or other indexing means so that depression of the finger press 62 controllably rotates the screw shaft 30 a desired amount. Preferably, the configuration of the prophy angle 10 is designed so that a single indexed radial advancement of the screw shaft by a single finger press corresponds with the discharge of a sensible amount of paste for use by the dental clinician. It need not do so, however, if it would be more desired to express or dispense a smaller or larger quantity for each manual trigger of the actuation means 60.

It is contemplated that the prophy angle 10 be pre-charged with paste during the production process so that it is shipped in a ready-to-use state. For example, the paste may be loaded into the primary chamber 32 prior to placement of the barrel plunger 54 and proximal wall 34 into the proximal end 16a of the distal member housing 16, or through the conduit 42 at the distal end 16b of the housing 16. Or a sealable opening may be provided in the proximal wall 34 or other location within the prophy angle proximal member 12 to permit injection of the paste into the chamber post-production, but prior to shipment. It is even contemplated that the clinician might load the paste into the primary chamber prior to use. The prophy angle may be designed for single use, or multiple use in which appropriate cleaning and/or sterilization methods are employed.

In one embodiment of the present invention, the components of the prophy angle are manufactured using sturdy but light weight materials, including but not limited to lightweight metals, or thermoplastics such as acrylonitrile butadiene styrene (ABS), polypropylene, polyethylene, polycarbonate or sturdy by lightweight material. However, other materials may be used. Indeed, alternative embodiments are contemplated without departing from the spirit of the invention described and claimed herein. Each of the components may be configured differently to accommodate a variety of sizes and arrangements while still maintaining the independence of the discharge of paste from the prophy cup drive mechanism. For example, the distal housing 16 need not include a tapered portion. In another example, the actuation means 60 may comprise a configuration in which the user's finger may engage the gear 50 directly to rotate the screw a set indexed amount. In yet another example, a lock means may be provided to preclude reverse direction of the screw shaft 30. These examples are not intended to be limiting. As such, the invention herein, as reflected by exemplary embodiments presented, should be measured by the claims set forth below.

What is claimed is:

1. A hand-held oral hygiene applicator for conveniently providing a clinician user the ability to express prophy paste while the applicator is in therapeutic use within a patient's mouth, the applicator comprising:
   a prophy angle housing comprising a distal end and a proximal end, the prophy angle housing configured to permit the clinician to conveniently handle the prophy angle housing at the proximal end while the distal end is placed within a patient's mouth during use, the prophy angle housing being further configured to permit the clinician to simultaneously control the expression of paste while providing the desired treatment to the patient, the housing further comprising a paste dispensing outlet proximal the distal end of the housing, the housing configured to permit securement of a rotatable head assembly to the housing concentrically with the paste dispensing outlet;
   a first drive mechanism positioned within the prophy angle housing comprising a drive shaft for delivering mechanical energy to the rotatable head assembly,
   a chamber substantially enclosed within the prophy angle housing, the chamber configured to store paste in a controlled releasable manner such that the paste is precluded from contacting the first drive mechanism, the chamber being configured to permit expression of paste by the clinician from the proximal end of the prophy angle housing; and
   an independent second drive mechanism provided within the prophy angle housing and positioned coaxially with the first drive mechanism, the second drive mechanism configured to deliver a controlled amount of paste from the chamber to the distal end of the prophy angle housing for as needed expression thereof to the patient by the clinician, the second drive mechanism comprising a shaft including a tapered helical blade at a distal end of the second drive mechanism and a helical thread at a proximal end of the second drive mechanism, the second drive mechanism further comprising an actuator positioned at or proximate the proximal end of the prophy angle housing, and a rotatable index wheel engaging the actuator so that the wheel may be driven in a stepped rotational manner upon actuation of the actuator by the clinician, the index wheel further engaging a barrel within the chamber where the barrel is rotatably supported and configured to be secured to and advance distally on the helical thread, the barrel axially exerting pressure against the paste within the chamber for delivering a controlled quantity of paste toward the distal end of the prophy angle, wherein the independent second drive mechanism operates independently from the first drive mechanism so that paste is dispensed as the clinician desires rather than continuously, regardless of actuation of the 1st drive mechanism.

2. The applicator of claim 1 wherein the chamber and helical thread are sized to deliver a pre-set amount of paste for each actuation of the actuator.

3. The applicator of claim 2 wherein the drive shaft of the first drive mechanism is positioned co-linearly with the helical thread and positioned therewithin.

4. The applicator of claim 1 wherein the chamber is configured to be rechargeable.

5. The applicator of claim 1 wherein the actuator comprises a finger press comprising a member for engaging the index wheel.

* * * * *